United States Patent [19]

Wehinger et al.

[11] Patent Number: 4,497,821

[45] Date of Patent: Feb. 5, 1985

[54] MEDICAMENTS HAVING ANTIHYPOXIC AND ISCHAEMIA-PROTECTIVE ACTIVITY

[75] Inventors: Egbert Wehinger; Horst Meyer, both of Wuppertal; Ulrich Benz, Duesseldorf, all of Fed. Rep. of Germany

[73] Assignee: Bayer Aktiengesellschaft, Leverkusen, Fed. Rep. of Germany

[21] Appl. No.: 470,883

[22] Filed: Feb. 28, 1983

[30] Foreign Application Priority Data

Mar. 13, 1982 [DE] Fed. Rep. of Germany ....... 3209276

[51] Int. Cl.³ .................... A61K 31/34; A61K 31/38; A61K 31/42; A61K 31/44; A61K 31/47; A61K 31/415; A61K 31/425; A61K 31/475; A61K 31/495; A61K 31/505
[52] U.S. Cl. ................................. 514/302; 514/334; 514/337; 514/338; 514/340; 514/341; 514/342; 514/343; 514/344; 514/355; 514/356; 514/348
[58] Field of Search ......................................... 424/263

Primary Examiner—Stanley J. Friedman
Attorney, Agent, or Firm—Sprung, Horn, Kramer & Woods

[57] ABSTRACT

A method of controlling damage to the central nervous system of a patient which comprises administering to such patient a central nervous system-controlling effective amount of a pyridine derivative of the formula

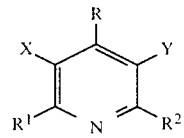

in which
R is an optionally substituted aryl or heterocyclic radical,
$R^1$ and $R^2$ are hydrogen or various organic radicals,
X and Y are CN, $-CO-R^3$, $-COOR^4$ or $-SO_2R^5$, or form with $R^1$ or $R^2$ a carbonyl-containing ring,
$R^3$ is an alkyl, aryl or aralkyl radical,
$R^4$ is hydrogen or an organic radical, and
$R^5$ is an optionally substituted alkyl or phenyl radical, or a salt thereof.

12 Claims, No Drawings

MEDICAMENTS HAVING ANTIHYPOXIC AND ISCHAEMIA-PROTECTIVE ACTIVITY

The present invention relates to the use of substituted pyridine derivatives, some of which are known, as medicaments for controlling damage to the central nervous system.

It has already been disclosed that diethyl 2,6-dimethyl-4-(2-nitrophenyl)pyridine-3,5-dicarboxylate is obtained by chromic acid oxidation of the corresponding diethyl 1,4-dihydro-2,6-dimethyl-4-(2-nitrophenyl)pyridine-3,5-dicarboxylate (see V. A. Petrow, J. Chem. Soc. 884 (1946)).

Furthermore, it has been disclosed that, during the biotransformation of 4-aryl-1,4-dihydropyridine derivatives having vasodilator activity, pyridines are produced which are substantially less vasoactive than the corresponding dihydropyridine compounds (see S. Higuchi et al. 95th General Congress of the Japanese Pharmaceutical Society, April 1975; S. E. Parker and J. Weinstock, J. Med. Chem. 16, 34 (1973)).

Furthermore, it has been disclosed that the compound isopropyl 2-methoxyethyl 1,4-dihydro-2,6-dimethyl-4-(3-nitrophenyl)pyridine-3,5-dicarboxylate can be employed for controlling cerebral insufficiency (see U.S. Ser. No. 346,319 filed Feb. 5, 1982, now pending.)

Furthermore, 4-(3-nitrophenyl)pyridine-3,5-dicarboxylic acid esters have been used as intermediate products in the synthesis of pyridylquinolones having antibacterial activity (P. M. Carbateas and G. L. Williams, J. Heterocyclic Chem. 11, 819 (1974)).

However, the use of pyridine derivatives of the general formula (I) as active pharmaceutical compounds, in particular for controlling damage to the central nervous system, which is due to ischaemia and/or hypoxia, is new and has not hitherto been disclosed.

It has been found that pyridine derivatives of the general formula (I)

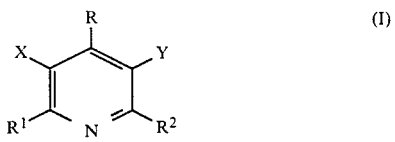
(I)

in which
R represents an aryl radical or a thienyl, furyl, pyrryl, pyrazolyl, imidazolyl, oxazolyl, isoxazolyl, thiazolyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl radical, the aryl radical and the heterocycles optionally containing 1 to 2 identical or different substituents from the group comprising phenyl, alkyl, alkoxy, alkylene, dioxyalkylene, halogen, trifluoromethyl, polyfluoroalkoxy, nitro, cyano, azido or $SO_m$-alkyl (m=0 to 2), $R^1$ and $R^2$ are identical or different and represent hydrogen, a straight chain or branched alkyl radical, an aryl radical or an aralkyl radical or represent an acyloxyalkyl or a hydroxyalkyl group, or represent an alkylene chain, which, together with X or Y, forms a 5 to 7-membered ring which contains a carbonyl group and optionally an oxygen or nitrogen atom, and X and Y are identical or different and represent the nitrile group or represent the radical $-CO-R^3$, $R^3$ representing a straight-chain, branched or cyclic alkyl radical, an aryl radical or an aralkyl radical, or X and Y represent the group $-COOR^4$, $R^4$ representing a hydrogen atom, a straight-chain, branched or cyclic, saturated or unsaturated hydrocarbon radical, which is optionally interrupted by an oxygen atom in the chain and/or is optionally substituted by halogen, cyano, hydroxyl, acyloxy, pyridyl, aryl or aryloxy, it being possible for the aryl groups in turn to be substituted by alkyl, fluorinated alkyl, alkoxy, halogen or nitro, or by an amino group which is optionally substituted by two identical or different substituents from the group comprising alkyl, aryl or aralkyl, or X and Y represent the group $-SO_2R^5$, $R^5$ representing a lower alkyl radical or a phenyl radical optionally substituted by halogen, trifluoromethyl, alkoxy or alkyl;

as such or in the form of their salts, exhibit strong antiamnesic effects.

Surprisingly, the compounds according to the invention exhibit a strong protective effect against hypoxia, which becomes manifest in hypoxia-induced amnesia and also in the tolerance of hypoxia. These specific pharmacological effects of the substituted pyridine compounds, which compounds are known from the state of the art, have not hitherto been disclosed, so that the compounds according to the invention are an enrichment of pharmacy in respect of these properties.

The compounds are either known or can be prepared in a simple manner by (a) reacting 1,4-dihydropyridine derivatives of the general formula (II)

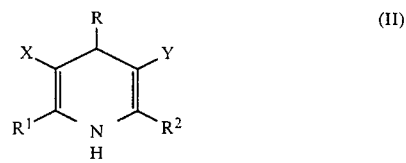
(II)

in which
R, $R^1$, $R^2$, X and Y have the meaning indicated above, with oxidizing (dehydrogenating) agents, optionally in the presence of inert solvents, at temperatures between 0° and 200° C., suitable oxidizing agents (dehydrogenating agents) being primarily nitric acid or nitrous acid, chromium(VI) oxide or sodium dichromate, nitrogen oxides, chloranil, tetracyanobenzoquinone or anodic oxidation in the presence of a suitable electrolyte system, or (b) if appropriate, interconverting the compounds according to the invention, by converting compounds according to the invention of the formula (III) with $R^4=H$,

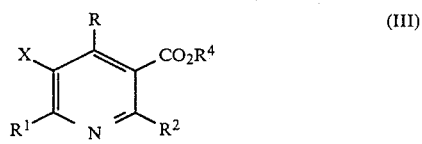
(III)

under the conditions of alkaline hydrolysis, into compounds according to the invention of the formula (III), with R⁴=H, or, conversely, reacting compounds according to the invention of the formula (III), with R⁴=H, by the methods known from the literature for esterification of carboxylic acids, to give compounds of the formula (III) with R⁴=H, or
(c) hydrolyzing substances according to the invention of the general formula (IV),

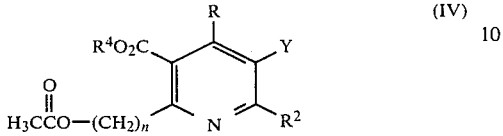

in which
R, R², R⁴ and Y have the meaning indicated above and
n represents a whole number from 1 to 4,
by known methods to give compounds of the formula (V)

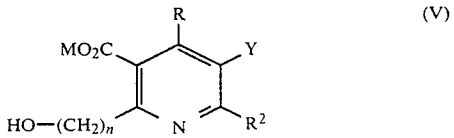

in which
R, R², Y and n have the meaning indicated above and
M represents alkali metal,
the corresponding lactone of the general formula (VI)

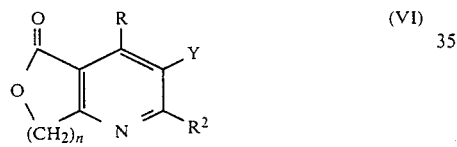

being produced in acid medium.

The foregoing preparation processes are only indicated for elucidation, and the preparation of the compounds of the formula (I) is not restricted to these processes.

The use of compounds according to the invention of the formula (I) is of particular significance

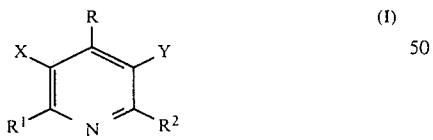

in which compounds
R represents a phenyl or naphthyl radical or represents a thienyl, furyl, pyrryl, pyrazolyl, imidazolyl, oxazolyl, isoxazolyl, thiazolyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl radical, the phenyl or naphthyl ring and the heterocycles optionally containing 1 to 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, tri-, tetra- or penta-methylene, dioxymethylene, dioxyethylene, fluorine, chlorine, bromine or iodine, trifluoromethyl, trifluoromethoxy, difluoromethoxy, tetrafluoroethoxy, nitro, cyano, azido or $SO_m$-alkyl, wherein m denotes a number from 0 to 2 and alkyl 1 to 4 carbon atoms, R¹ and R² are identical or different and represent hydrogen or represent a straight-chain or branched alkyl radical having 1 to 8 carbon atoms or represent a phenyl radical or a benzyl radical or represent the acetoxymethyl or 2-acetoxyethyl radical or represent a hydroxyalkyl group having up to 4 carbon atoms in the alkyl moiety, or represent an alkylene chain, having 1 to 3 carbon atoms which is optionally substituted by alkyl (1 to 4 C atoms) which chain, together with X or Y, forms a 5 to 7-membered ring, which contains a carbonyl group and optionally an oxygen or nitrogen atom, the nitrogen optionally still carrying a hydrogen atom or a lower alkyl radical (1 to 4 C atoms), and X and Y are identical or different and represent the nitrile group or represent the radical —COR³, R³ representing a straight-chain, branched or cyclic alkyl radical having 1 to 8 carbon atoms, or the phenyl group or the benzyl group, or X and Y represent the group —COOR⁴, R⁴ representing a hydrogen atom, a straight-chain, branched or cyclic, saturated or unsaturated hydrocarbon radical having up to 12 carbon atoms which is optionally interrupted by one oxygen atom in the chain and/or is optionally substituted by fluorine, chlorine, bromine, cyano, hydroxyl, acetoxy, α-, β- or γ-pyridyl, phenyl, phenoxy or naphthoxy, it being possible for the aryl groups in turn to be substituted by lower alkyl (1 to 4 C atoms), trifluoromethyl, lower alkoxy (1 to 4 atoms), fluorine or chlorine or nitro, or by an amino group which is optionally substituted by two identical or different substituents from the group comprising alkyl having 1 to 2 carbon atoms, phenyl or benzyl, or X and Y represent the group —SO₂R⁵, R⁵ representing a lower alkyl radical having 1 to 8 carbon atoms or a phenyl group which is optionally substituted by fluorine, chlorine, trifluoromethyl, or alkyl or alkoxy having, in each case, 1 to 4 carbon atoms.

The use of compounds of the general formula (I) is of particular interest, in which compounds R represents phenyl or pyridyl, the phenyl radical optionally being substituted once or twice by nitro, cyano, trifluoromethyl, fluorine, chlorine, bromine, iodine, or alkyl, alkoxy or alkylmercapto having, in each case, 1 to 2 C atoms in the alkyl and alkoxy radicals, R¹ and R² are identical or different and represent, in each case, hydrogen or an alkyl radical having 1 to 4 carbon atoms which is optionally substituted by hydroxyl, or R¹ together with X or R² together with Y together form a 5 to 7-membered ring which is interrupted by carbonyl and optionally by oxygen and/or NH and X and Y are identical or different and each represent a nitrile group or X and Y represent the radical —COR³, R³ denoting an alkyl radical having 1 to 4 carbon atoms, phenyl or benzyl or X and Y represent the group —COOR⁴, $R^4$ denoting hydrogen, a straight-chain, branched or cyclic saturated or unsaturated hydrocarbon radical having up to 10 carbon atoms which is optionally interrupted by 1 oxygen atom in the chain and/or is optionally substituted by hydroxyl, fluorine, chlorine, bromine, cyano, acetoxy, pyridyl, phenyl or phenoxy, it being possible for the phenyl groups in turn to be optionally substituted by fluorine, chlorine, trifluoromethyl, nitro, alkyl having 1 to 4 C atoms or alkoxy having 1 to 4 C atoms, or X and Y represent the group —SO₂R⁵, $R^5$ representing an alkyl radical having 1 to 4 carbon atoms or a phenyl group which is optionally substituted by fluorine, chlorine, trifluoromethyl, or alkyl or alkoxy having, in each case, 1 to 2 carbon atoms.

Apart from the examples detailed below, the following active compounds according to the invention may be mentioned: 2-hydroxyethyl methyl 2,6-dimethyl-4-(2-nitrophenyl)pyridine-3,5-dicarboxylate, 2-hydroxyethyl ethyl 2,6-dimethyl-4-(2-nitrophenyl)pyridine-3,5-dicarboxylate, 2-hydroxyethyl isobutyl 2,6-dimethyl-4-(2-nitrophenyl)pyridine-3,5-dicarboxylate, 2-hydroxyethyl cyclopentyl 2,6-dimethyl-4-(2-nitrophenyl)pyridine-3,5-dicarboxylate, 3-hydroxypropyl isopropyl 2,6-dimethyl-4-(3-nitrophenyl)pyridine-3,5-dicarboxylate, 3-acetoxypropyl isopropyl 2,6-dimethyl-4-(3-nitrophenyl)pyridine-3,5-dicarboxylate, 3-chloropropyl isopropyl 2,6-dimethyl-4-(3-nitrophenyl)pyridine-3,5-dicarboxylate, 3-cyanopropyl isopropyl 2,6-dimethyl-4-(3-nitrophenyl)pyridine-3,5-dicarboxylate, 4-hydroxybutyl isopropyl 2,6-dimethyl-4-(3-nitrophenyl)pyridine-3,5-dicarboxylate, 2-hydroxyethyl benzyl 2,6-dimethyl-4-(3-nitrophenyl)pyridine-3,5-dicarboxylate, 2-hydroxyethyl 2,2,2-trifluoroethyl 2,6-dimethyl-4-(3-nitrophenyl)pyridine-3,5-dicarboxylate, 2-hydroxyethyl 2,6-dimethyl-4-(3-nitrophenyl)-3-acetylpyridine-5-carboxylate, 2-acetoxyethyl 2,6-dimethyl-4-(3-nitrophenyl)-3-acetylpyridine-5-carboxylate, 2-chloroethyl 2,6-dimethyl-4-(3-nitrophenyl)-3-acetylpyridine-5-carboxylate, 2-hydroxyethyl isopropyl 2,6-dimethyl-4-(2-chlorophenyl)pyridine-3,5-dicarboxylate, 2-hydroxyethyl isopropyl 2,6-dimethyl-4-(2,3-dichlorophenyl)pyridine-3,5-dicarboxylate, 2-hydroxyethyl methyl 2,6-dimethyl-4-(2,3-dichlorophenyl)pyridine-3,5-dicarboxylate, 2-hydroxyethyl isopropyl 2,6-dimethyl-4-(3-pyridyl)pyridine-3,5-dicarboxylate, 2-hydroxyethyl isopropyl 2,6-dimethyl-4-(2-pyridyl)pyridine-3,5-dicarboxylate, 2-hydroxyethyl isopropyl 2,6-dimethyl-4-(2-methylthio-3-pyridyl)pyridine-3,5-dicarboxylate, 2-hydroxyethyl isopropyl 2,6-dimethyl-4-(2,1,3-benzoxadiazol-4-yl)pyridine-3,5-dicarboxylate, 2-hydroxyethyl methyl 2,6-dimethyl-4-(2,1,3-benzoxadiazol-4-yl)pyridine-3,5-dicarboxylate, 3-(2-hydroxyethyl) 5-isopropyl 6-hydroxymethyl-2-methyl-4-(3-nitrophenyl)pyridine-3,5-dicarboxylate, 3-(2-cyanoethyl) 5-isopropyl 6-hydroxymethyl-2-methyl-4-(3-nitrophenyl)pyridine-3,5-dicarboxylate, methyl 5,7-dihydro-2-methyl-4-(2-nitrophenyl)-5-oxofuro[3,4-b]pyridine-3-carboxylate, ethyl 5,7-dihydro-2-methyl-4-(2-trifluoromethylphenyl)-5-oxofuro[3,4-b]pyridine-3-carboxylate and methyl 5,7-dihydro-2-methyl-4-(3-pyridyl)-5-oxofuro[3,4-b]pyridine-3-carboxylate.

The compounds mentioned are particularly suitable for the treatment of hypoxic and/or ischaemic damage, principally of the central nervous system, and of sclerotic, necrotic or age-related cerebral insufficiency and psychopathological states.

The advantageous properties are demonstrated by the following investigations.

(a) Protective action against hypoxia in the model of hypoxia-induced retrograde amnesia in the passive avoidance test (Compare S. J. Sara and D. Lefevre, Psychopharmakologia, 25, 32–40, 1972)

In a cage having light and dark sections, rats are trained, using an electroshock, to avoid the dark section of the cage. When the experimental animals are then exposed to a hypoxia atmosphere (3.5% by volume of $O_2$), the contents of the memory are retroactively destroyed. The abovementioned compounds antagonize retrograde amnesia completely (1 mg/kg of body weight p.o. 30 min. before hypoxia).

(b) Increase in tolerance of hypoxia

Mice treated with substance or placebo are placed in a chamber through which a hypoxic gas mixture (3.5% by volume of $O_2$) is passed until 85% of the control animals are dead. The abovementioned compounds significantly increase the number of surviving animals (10 mg/kg of body weight 30 min. before hypoxia).

(c) Inhibition of defensive behavior

Mice, which have been kept isolated, show "aggressive-defensive behavior" on electrical provocation. The compounds according to the invention, which are otherwise without general sedative effects, completely inhibit this behavior.

The compounds mentioned have a strong protective action against hypoxia, although they affect neither the blood pressure nor the heart rate, nor are they vasoactive on isolated strips of rabbit vascular tissue. The psychotropic effect shown is of additional therapeutic significance, particularly in gerontology.

The new active compounds can be converted, in a known manner, into the customary formulations, such as tablets, capsules, coated tablets, pills, granules, aerosols, syrups, emulsions, suspensions and solutions, using inert, non-toxic pharmaceutically suitable vehicles or solvents. The therapeutically active compound, may, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example when using water as the diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid vehicles, such as, for example, natural rock powder (for example kaolins, aluminas, talc and chalk), synthetic rock powders (for example highly disperse silica (silicates), sugars (for example cane sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc, can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.01 to 10 mg/kg, preferably about 0.1 to 5 mg/kg of body weight daily to achieve effective results; in the case of oral administration, the dose is about 0.05 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus it may suffice in some cases to manage with less than the abovementioned minimum amount, while in other cases the upper limit mentioned must be exceeded. Where relatively large amounts are administered, it can be advisable to divide these into several individual administrations during the course of the day. The same dosage range is envisaged for administration in human medicine. In this connection, the above statements similarly apply.

PREPARATION EXAMPLES

Example 1

2-Hydroxyethyl isopropyl 2,6-dimethyl-4-(3-nitrophenyl)pyridine-3,5-dicarboxylate

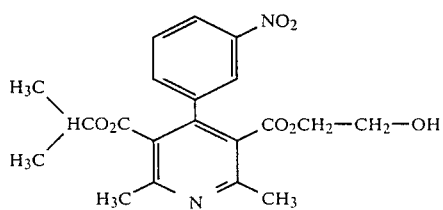

20 g (49.5 mmol) of 2-hydroxyethyl isopropyl 1,4-dihydro-2,6-dimethyl-4-(3-nitrophenyl)pyridine-3,5-dicarboxylate were introduced into a mixture of 83 ml of 96% strength nitric acid in 660 ml of water and heated to boiling for 1 hour. The mixture was then cooled down to 5° to 10° C. and made weakly alkaline with dilute sodium hydroxide solution. The oil which had separated out was extracted with methylene chloride, the extracts were dried over sodium sulphate and evaporated in vacuo. The oily residue was induced to crystallize by trituration with ether/petroleum ether, filtered off with suction and recrystallized from methanol.

Melting point: 120° C. Yield: 13.1 g (66%)

Example 2

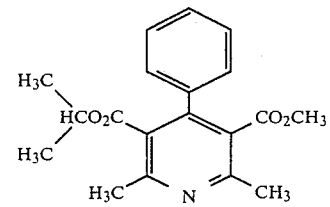

Isopropyl methyl 2,6-dimethyl-4-phenylpyridine-3,5-dicarboxylate, of melting point: 55° C., was obtained in analogy to Example 1 by reaction of isopropyl methyl 1,4-dihydro-2,6-dimethyl-4-phenylpyridine-3,5-dicarboxylate with nitric acid.

Yield: 72% of theory.

Example 3

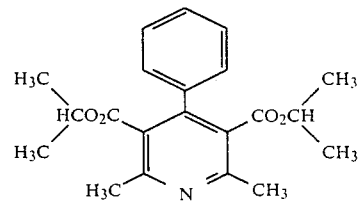

Diisopropyl 2,6-dimethyl-4-phenylpyridine-3,5-dicarboxylate, of melting point 107° C., was obtained in analogy to Example 1 by reaction of diisopropyl 1,4-dihydro-2,6-dimethyl-4-phenylpyridine-3,5-dicarboxylate with nitric acid.

Yield: 61% of theory.

Example 4

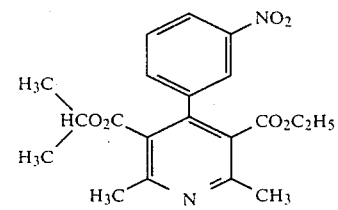

Ethyl isopropyl 2,6-dimethyl-4-(3-nitrophenyl)pyridine-3,5-dicarboxylate, of melting point 64° C., was obtained in analogy to Example 1 by reaction of ethyl isopropyl 1,4-dihydro-2,6-dimethyl-4-(3-nitrophenyl)-pyridine-3,5-dicarboxylate with nitric acid.

Yield: 68% of theory.

Example 5

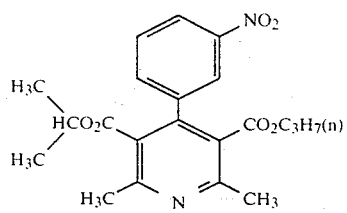

Isopropyl propyl 2,6-dimethyl-4-(3-nitrophenyl)pyridine-3,5-dicarboxylate, of melting point 48° C., was obtained in analogy to Example 1 by reaction of isopropyl propyl 1,4-dihydro-2,6-dimethyl-4-(3-nitrophenyl)-pyridine-3,5-dicarboxylate with nitric acid.

Yield: 75% of theory.

Example 6

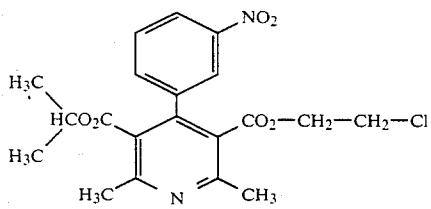

2-Chloroethyl isopropyl 2,6-dimethyl-4-(3-nitrophenyl)pyridine-3,5-dicarboxylate, of melting point 80° C., was obtained in analogy to Example 1 by reaction of 2-chloroethyl isopropyl 1,4-dihydro-2,6-dimethyl-4-(3-nitrophenyl)pyridine-3,5-dicarboxylate with nitric acid.

Yield: 69% of theory.

Example 7

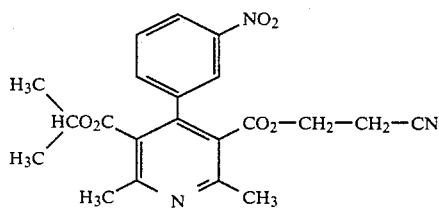

2-Cyanoethyl isopropyl 2,6-dimethyl-4-(3-nitrophenyl)pyridine-3,5-dicarboxyl, of melting point 93° C., was obtained in analogy to Example 1 by reaction of 2-cyanoethyl isopropyl 1,4-dihydro-2,6-dimethyl-4-(3-nitrophenyl)pyridine-3,5-dicarboxylate with nitric acid.

Yield: 71% of theory.

Example 8

2-Acetoxyethyl isopropyl 2,6-dimethyl-4-(3-nitrophenyl)pyridine-3,5-dicarboxylate

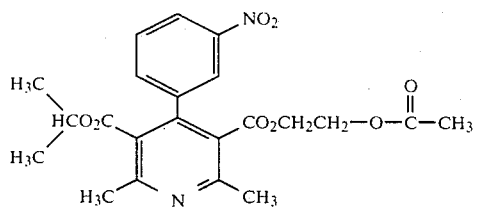

20.1 g (50 mmols) of 2-hydroxyethyl isopropyl 2,6-dimethyl-4-(3-nitrophenyl)pyridine-3,5-dicarboxylate (Example 1) were dissolved in 75 ml of pyridine. 5.9 g (75 mmoles) of acetyl chloride were added to this. After the exothermic reaction was over, the reaction mixture was stirred at room temperature for 3 hours, poured into water and extracted with $CH_2Cl_2$. The organic extracts were washed with dilute hydrochloric acid and, after drying over sodium sulphate, evaporated in vacuo. The resulting oil crystallized completely, it was stirred with petroleum ether, filtered off with suction and dried.

Melting point 68° C., yield: 20.5 g (93%).

Example 9

Isopropyl 2-methoxyethyl 2,6-dimethyl-4-(3-nitrophenyl)pyridine-3,5-dicarboxylate

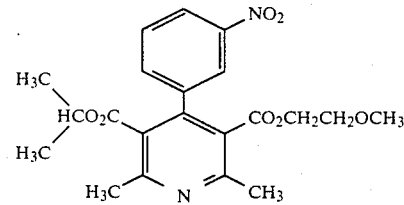

6.8 g of chromium(VI) oxide were added in portions to a boiling solution of 41.8 g (100 mmols) of isopropyl 2-methoxyethyl 1,4-dihydro-2,6-dimethyl-4-(3-nitrophenyl)pyridine-3,5-dicarboxylate in 160 ml of glacial acetic acid. The mixture was then heated under reflux for a further 30 minutes and, after cooling down, poured into ammoniacal ice-water. The mixture was extracted with chloroform and the extracts, after drying over sodium sulphate, were evaporated in vacuo. 35.9 g (86% of theory) of an oil resulted.

Example 10

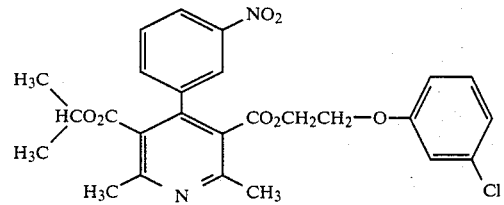

2-(3-Chlorophenoxy)ethyl isopropyl 2,6-dimethyl-4-(3-nitrophenyl)pyridine-3,5-dicarboxylate, of melting point 79° C., was obtained in analogy to Example 1 by reaction of 2-(3-chlorophenoxy)ethyl isopropyl 1,4-dihydro-2,6-dimethyl-4-(3-nitrophenyl)pyridine-3,5-dicarboxylate with nitric acid.

Yield: 85% of theory.

Example 11

2,6-Dimethyl-4-(3-nitrophenyl)pyridine-3,5-dicarboxylic acid monoisopropyl ester

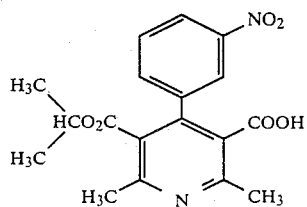

1 g (2.5 mmols) of diisopropyl 2,6-dimethyl-4-(3-nitrophenyl)pyridine-3,5-dicarboxylate was heated under reflux for 5 hours in a solution of 140 mg (2.5 mmols) of potassium hydroxide in 10 ml of ethanol and 1 ml of water. After cooling down, the mixture was evaporated to dryness, the residue was taken up in water and extracted several times with chloroform. The aqueous phase was adjusted to pH 3 to 4 with dilute hydrochloric acid, the precipitated product was filtered off with suction and dissolved again with saturated sodium bicarbonate solution. After adding a little animal charcoal, the mixture was filtered and the filtrate was adjusted to pH 3 to 4 with dilute hydrochloric acid. The precipitated product was filtered off with suction and dried in vacuo.

Melting point 234°–236° C. Yield: 300 mg (33% of theory).

Example 12

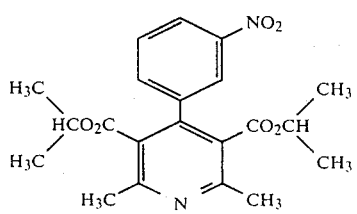

Diisopropyl 2,6-dimethyl-4-(3-nitrophenyl)pyridine-3,5-dicarboxylate, of melting point 77° C., was obtained in analogy to Example 1 by reaction of diisopropyl 1,4-dihydro-2,6-dimethyl-4-(3-nitrophenyl)pyridine-3,5-dicarboxylate with nitric acid.

Yield: 66% of theory.

Example 13

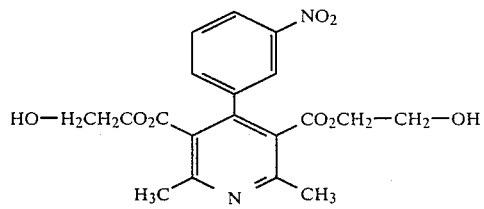

Bis(2-hydroxyethyl) 2,6-dimethyl-4-(3-nitrophenyl)pyridine-3,5-dicarboxylate, of melting point 121° C., was obtained in analogy to Example 1 by reaction of bis(2-hydroxyethyl) 1,4-dihydro-2,6-dimethyl-4-(3-nitrophenyl)pyridine-3,5-dicarboxylate with nitric acid.

Yield: 81% of theory.

Example 14

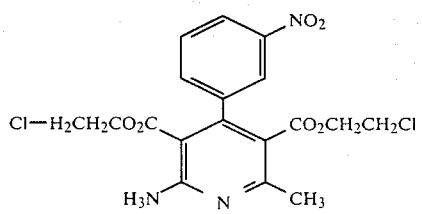

Bis(2-chloroethyl) 2,6-dimethyl-4-(3-nitrophenyl)pyridine-3,5-dicarboxylate, of melting point 72° C., was obtained in analogy to Example 1 by reaction of bis(2-chloroethyl) 1,4-dihydro-2,6-dimethyl-4-(3-nitrophenyl)pyridine-3,5-dicarboxylate with nitric acid.

Yield: 80% of theory.

Example 15

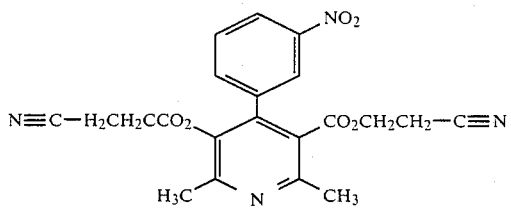

Bis(2-cyanoethyl) 2,6-dimethyl-4-(3-nitrophenyl)pyridine-3,5-dicarboxylate, of melting point 130° C., was obtained in analogy to Example 1 by reaction of bis(2-cyanoethyl) 1,4-dihydro-2,6-dimethyl-4-(3-nitrophenyl)pyridine-3,5-dicarboxylate with nitric acid.

Yield: 65% of theory.

Example 16

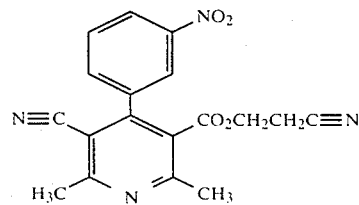

2-Cyanoethyl 3-cyano-2,6-dimethyl-4-(3-nitrophenyl)pyridine-5-carboxylate, of melting point 142° C., was obtained in analogy to Example 1 by reaction of 2-cyanoethyl 3-cyano-1,4-dihydro-2,6-dimethyl-4-(3-nitrophenyl)pyridine-5-carboxylate with nitric acid.

Yield: 69% of theory.

Example 17

2-Cyanoethyl 3-acetyl-2,6-dimethyl-4-(3-nitrophenyl)pyridine-5-carboxylate

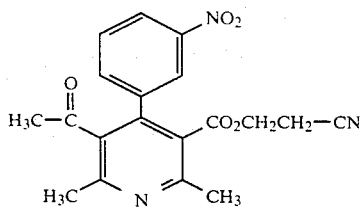

A solution of 10 g (27 mmols) of 2-cyanoethyl 3-acetyl-1,4-dihydro-2,6-dimethyl-4-(3-nitrophenyl)-pyridine-5-carboxylate in an electrolyte of 5 g of lithium perchlorate in 250 ml of acetonitrile was electrolyzed on a platinum anode at an electrode potential of +1.2 V vs. SCE. After passing through 2 Faraday equivalents, the electrolysis was stopped, the anolyte was evaporated in vacuo, the residue was taken up in a sodium bicarbonate solution and extracted several times with methylene chloride. The organic extracts were washed with water, dried over sodium sulphate and then evaporated in vacuo. The resulting oil crystallized completely, and the solid product was thoroughly stirred in petroleum ether, filtered off with suction and dried, melting point 85° C., yield: 7.5 g (75%).

Example 18

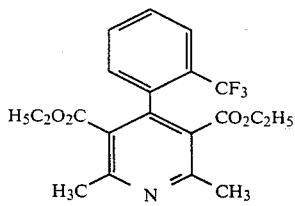

Diethyl 2,6-dimethyl-4-(2-trifluoromethylphenyl)-pyridine-3,5-dicarboxylate, of melting point 92° C., was obtained in analogy to Example 17 by anodic oxidation of diethyl 1,4-dihydro-2,6-dimethyl-4-(2-trifluoromethylphenyl)pyridine-3,5-dicarboxylate in acetonitrile/LiClO$_4$.

Yield: 83% of theory.

Example 19

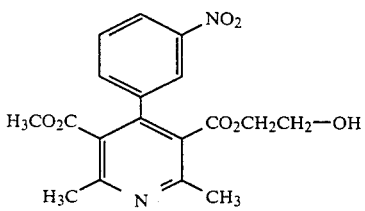

2-Hydroxyethyl methyl 2,6-dimethyl-4-(3-nitrophenyl)pyridine-3,5-dicarboxylate, of melting point 115° C., was obtained in analogy to Example 1 by reaction of 2-hydroxyethyl methyl 1,4-dihydro-2,6-dimethyl-4-(3-nitrophenyl)pyridine-3,5-dicarboxylate with nitric acid.

Yield: 59% of theory.

Example 20

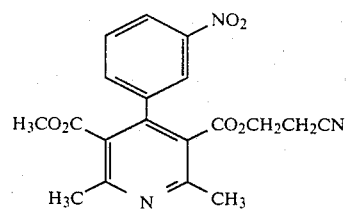

2-Cyanoethyl methyl 2,6-dimethyl-4-(3-nitrophenyl)-pyridine-3,5-dicarboxylate, of melting point 98° C., was obtained in analogy to Example 1 by reaction of 2-cyanoethyl methyl 1,4-dihydro-2,6-dimethyl-4-(3-nitrophenyl)pyridine-3,5-dicarboxylate with nitric acid.

Yield: 65% of theory.

Example 21

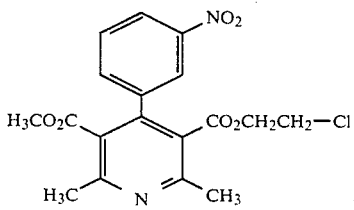

2-Chloroethyl methyl 2,6-dimethyl-4-(3-nitrophenyl)pyridine-3,5-dicarboxylate, of melting point 60° C., was obtained in analogy to Example 1 by reaction of 2-chloroethyl methyl 1,4-dihydro-2,6-dimethyl-4-(3-nitrophenyl)pyridine-3,5-dicarboxylate with nitric acid.

Yield: 55% of theory.

Example 22

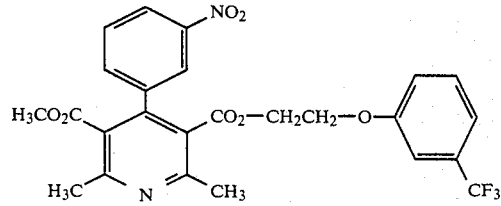

Methyl 2-(3-trifluoromethylphenoxy) 2,6-dimethyl-4-(3-nitrophenyl)pyridine-3,5-dicarboxylate, of melting point 88° C., was obtained in analogy to Example 1 by reaction of methyl 2-(3-trifluoromethylphenoxy)ethyl 1,4-dihydro-2,6-dimethyl-4-(3-nitrophenyl)pyridine-3,5-dicarboxylate with nitric acid.

Yield: 89% of theory.

Example 23

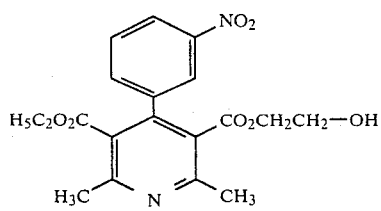

Ethyl 2-hydroxyethyl 2,6-dimethyl-4-(3-nitrophenyl)pyridine-3,5-dicarboxylate, of melting point 88° C., was obtained in analogy to Example 1 by reaction of ethyl 2-hydroxyethyl 1,4-dihydro-2,6-dimethyl-4-(3-nitrophenyl)pyridine-3,5-dicarboxylate with nitric acid.

Yield: 51% of theory.

Example 24

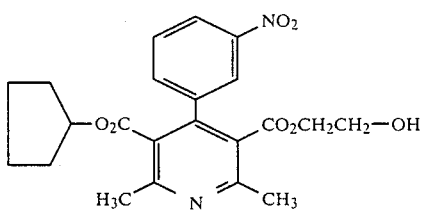

Cyclopentyl 2-hydroxyethyl 2,6-dimethyl-4-(3-nitrophenyl)pyridine-3,5-dicarboxylate, of melting point 112° C., was obtained in analogy to Example 1 by reaction of cyclopentyl 2-hydroxyethyl 1,4-dihydro-2,6-dimethyl-4-(3-nitrophenyl)pyridine-3,5-dicarboxylate with nitric acid.

Yield: 63% of theory.

Example 25

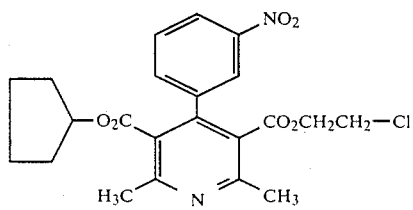

2-Chloroethyl cyclopentyl 2,6-dimethyl-4-(3-nitrophenyl)pyridine-3,5-dicarboxylate, of melting point 84° C., was obtained in analogy to Example 1 by reaction of 2-chloroethyl cyclopentyl 1,4-dihydro-2,6-dimethyl-4-(3-nitrophenyl)pyridine-3,5-dicarboxylate with nitric acid.

Yield: 71% of theory.

Example 26

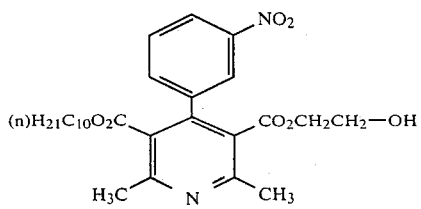

Decyl 2-hydroxyethyl 2,6-dimethyl-4-(3-nitrophenyl)pyridine-3,5-dicarboxylate, of melting point 60° C., was obtained in analogy to Example 1 by reaction of decyl 2-hydroxyethyl 1,4-dihydro-2,6-dimethyl-4-(3-nitrophenyl)pyridine-3,5-dicarboxylate with nitric acid.

Yield: 71% of theory.

Example 27

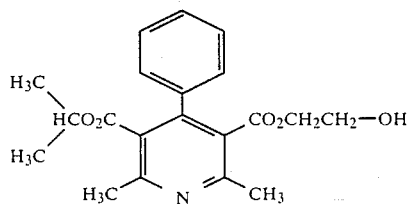

2-Hydroxyethyl isopropyl 2,6-dimethyl-4-phenyl-pyridine-3,5-dicarboxylate, of melting point 79° C., was obtained in analogy to Example 1 by reaction of 2-hydroxyethyl isopropyl 1,4-dihydro-2,6-dimethyl-4-phenylpyridine-3,5-dicarboxylate with nitric acid.

Yield: 82% of theory.

Example 28

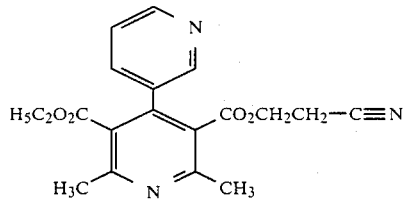

2-Cyanoethyl ethyl 2,6-dimethyl-4-(3-pyridyl)pyridine-3,5-dicarboxylate, of melting point 90° C., was obtained in analogy to Example 1 by reaction of 2-cyanoethyl ethyl 1,4-dihydro-2,6-dimethyl-4-(3-pyridyl)pyridine-3,5-dicarboxylate with nitric acid.

Yield 52% of theory.

Example 29

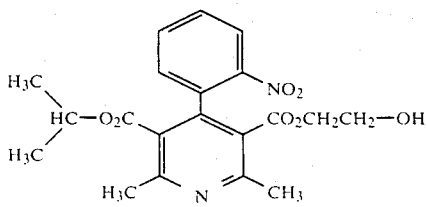

2-Hydroxyethyl isopropyl 2,6-dimethyl-4-(2-nitrophenyl)pyridine-3,5-dicarboxylate, of melting point 78° C., was obtained in analogy to Example 1, by reaction of 2-hydroxyethyl isopropyl 1,4-dihydro-2,6-dimethyl-4-(2-nitrophenyl)pyridine-3,5-dicarboxylate with nitric acid.

Yield 83%

Example 30

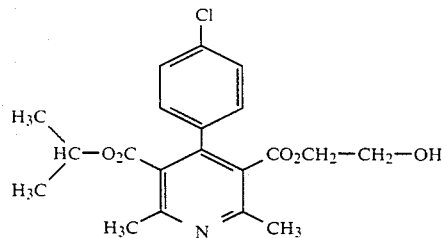

2-Hydroxyethyl isopropyl 2,6-dimethyl-4-(4-chlorophenyl)pyridine-3,5-dicarboxylate, of melting point 120° C., was obtained in analogy to Example 1 by reaction of 2-hydroxyethyl isopropyl 1,4-dihydro-2,6-dimethyl-4-(4-chlorophenyl)pyridine-3,5-dicarboxylate with nitric acid.

Yield 88% of theory.

Example 31

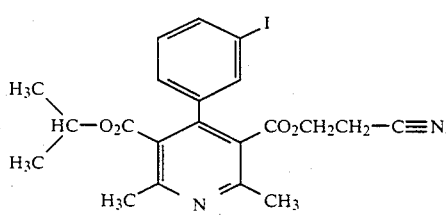

2-Cyanoethyl isopropyl 2,6-dimethyl-4-(3-iodophenyl)pyridine-3,5-dicarboxylate, of melting point 69° C., was obtained in analogy to Example 1 by reaction of 2-cyanoethyl isopropyl 1,4-dihydro-2,6-dimethyl-4-(3-iodophenyl)pyridine-3,5-dicarboxylate with nitric acid.

Yield 75% of theory.

EXAMPLE 32

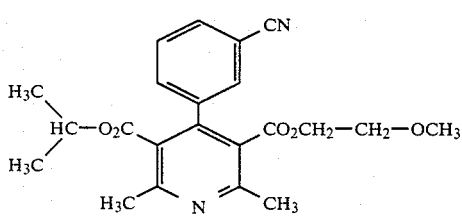

Isopropyl 2-methoxyethyl 2,6-dimethyl-4-(3-cyanophenyl)pyridine-3,5-dicarboxylate, of melting point 50° C., was obtained in analogy to Example 1 by reaction of isopropyl 2-methoxyethyl 1,4-dihydro-2,6-dimethyl-4-(3-cyanophenyl)pyridine-3,5-dicarboxylate with nitric acid.

Yield 73% of theory

Example 33

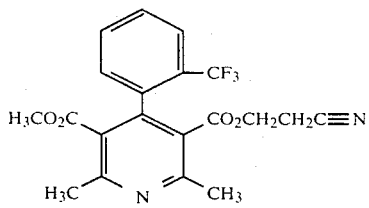

2-Cyanoethyl methyl 2,6-dimethyl-4-(2-trifluoromethylphenyl)pyridine-3,5-dicarboxylate, of melting point 74° C., was obtained in analogy to Example 1 by reaction of 2-cyanoethyl methyl 1,4-dihydro-2,6-dimethyl-4-(2-trifluoromethylphenyl)pyridine-3,5-dicarboxylate with nitric acid.

Yield 85% of theory

Example 34

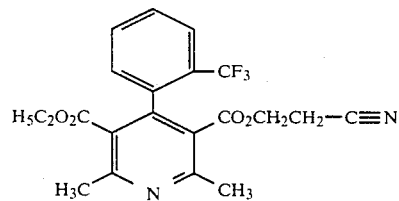

2-Cyanoethyl ethyl 2,6-dimethyl-4-(2-trifluoromethylphenyl)pyridine-3,5-dicarboxylate, of melting point 68° C., was obtained in analogy to Example 1 by reaction of 2-cyanoethyl ethyl 1,4-dihydro-2,6-dimethyl-4-(2-trifluoromethylphenyl)pyridine-3,5-dicarboxylate with nitric acid.

Yield 69% of theory.

Example 35

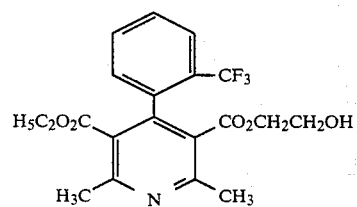

Ethyl 2-hydroxyethyl 2,6-dimethyl-4-(2-trifluoromethylphenyl)pyridine-3,5-dicarboxylate, of melting point 86° C., was obtained in analogy to Example 1 by reaction of ethyl 2-hydroxyethyl 1,4-dihydro-2,6-dimethyl-4-(2-trifluoromethylphenyl)pyridine-3,5-dicarboxylate with nitric acid.

Yield 75% of theory

Example 36

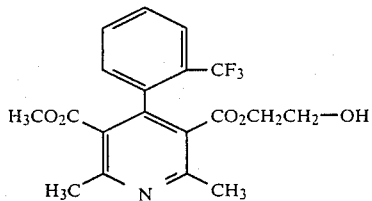

2-Hydroxyethyl methyl 2,6-dimethyl-4-(2-trifluoromethylphenyl)pyridine-3,5-dicarboxylate, of melting point 75° C., was obtained in analogy to Example 1 by reaction of 2-hydroxyethyl methyl 1,4-dihydro-2,6-dimethyl-4-(2-trifluoromethylphenyl)pyridine-3,5-dicarboxylate with nitric acid.

Yield 71% of theory

Example 37

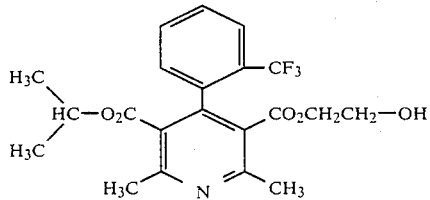

2-Hydroxyethyl isopropyl 2,6-dimethyl-4-(2-trifluoromethylphenyl)pyridine-3,5-dicarboxylate, of melting point 83° C., was obtained in analogy to Example 1 by reaction of 2-hydroxyethyl isopropyl 1,4-dihydro-2,6-dimethyl-4-(2-trifluoromethylphenyl)pyridine-3,5-dicarboxylate with nitric acid.

Yield 51% of theory.

Example 38

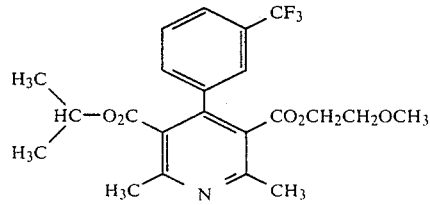

Isopropyl 2-methoxyethyl 2,6-dimethyl-4-(3-trifluoromethylphenyl)pyridine-3,5-dicarboxylate, of melting point 51° C., was obtained in analogy to Example 1 by reaction of isopropyl 2-methoxyethyl 1,4-dihydro-2,6-dimethyl-4-(3-trifluoromethylphenyl)pyridine-3,5-dicarboxylate with nitric acid.

Yield: 65% of theory.

Example 39

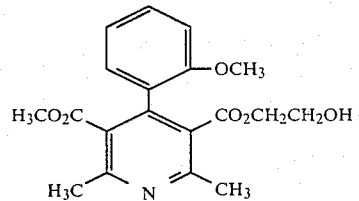

2-Hydroxyethyl methyl 2,6-dimethyl-4-(2-methoxyphenyl)pyridine-3,5-dicarboxylate, of melting point 90° C., was obtained in analogy to Example 1 by reaction of 2-hydroxyethyl methyl 1,4-dihydro-2,6-dimethyl-4-(2-methoxyphenyl)pyridine-3,5-dicarboxylate with nitric acid.

Yield 84% of theory.

Example 40

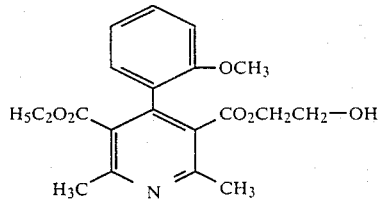

Ethyl 2-hydroxyethyl 2,6-dimethyl-4-(2-methoxyphenyl)pyridine-3,5-dicarboxylate, of melting point 95° C. was obtained in analogy to Example 1 by reaction of ethyl 2-hydroxyethyl 1,4-dihydro-2,6-dimethyl-4-(2-methoxyphenyl)pyridine-3,5-dicarboxylate with nitric acid.

Yield 71% of theory.

Example 41

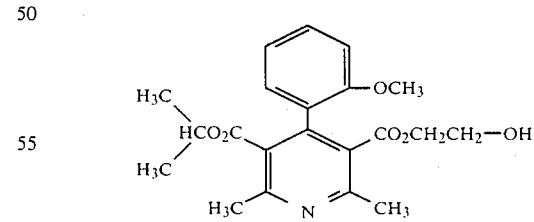

2-Hydroxyethyl isopropyl 2,6-dimethyl-4-(2-methoxyphenyl)pyridine-3,5-dicarboxylate, of melting point 68° C., was obtained in analogy to Example 1 by reaction of 2-hydroxyethyl isopropyl 1,4-dihydro-2,6-dimethyl-4-(2-methoxyphenyl)pyridine-3,5-dicarboxylate with nitric acid.

Yield 85% of theory.

Example 42

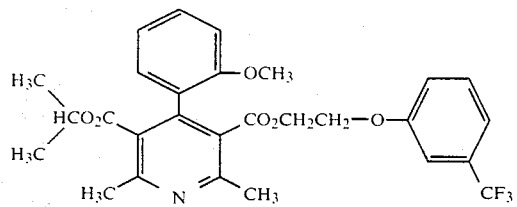

Isopropyl 2-(3-trifluoromethylphenoxy)ethyl 2,6-dimethyl-4-(2-methoxyphenyl)pyridine-3,5-dicarboxylate, of melting point 80° C., was obtained in analogy to Example 1 by reaction of isopropyl 2-(3-trifluoromethylphenoxy)ethyl 1,4-dihydro-2,6-dimethyl-4-(2-methoxyphenyl)pyridine-3,5-dicarboxylate with nitric acid.

Yield 65% of theory.

Example 43

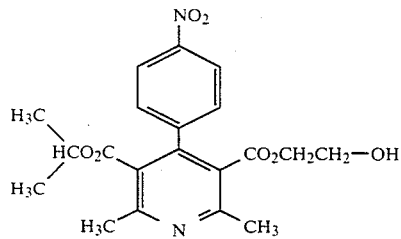

2-Hydroxyethyl isopropyl 2,6-dimethyl-4-(4-nitrophenyl)pyridine-3,5-dicarboxylate, of melting point 145° C., was obtained in analogy to Example 1 by reaction of 2-hydroxyethyl isopropyl 1,4-dihydro-2,6-dimethyl-4-(4-nitrophenyl)pyridine-3,5-dicarboxylate with nitric acid.

Yield 62% of theory.

Example 44

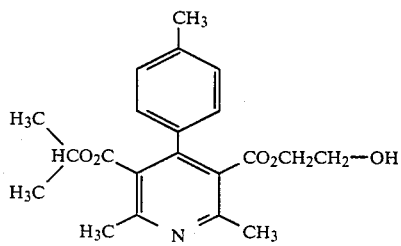

2-Hydroxyethyl isopropyl 2,6-dimethyl-4-(4-methylphenyl)pyridine-3,5-dicarboxylate, of melting point 72° C., was obtained in analogy to Example 1 by reaction of 2-hydroxyethyl isopropyl 1,4-dihydro-2,6-dimethyl-4-(4-methylphenyl)pyridine-3,5-dicarboxylate with nitric acid.

Yield 56% of theory.

Example 45

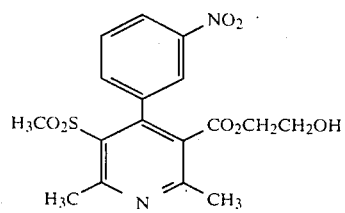

2-Hydroxyethyl 2,6-dimethyl-3-methylsulphonyl-4-(3-nitrophenyl)pyridine-5-carboxylate of melting point 120° C., was obtained in analogy to Example 1 by reaction of 2-hydroxyethyl 1,4-dihydro-2,6-dimethyl-3-methylsulphonyl-4-(3-nitrophenyl)pyridine-5-carboxylate with nitric acid.

Yield 53% of theory.

Example 46

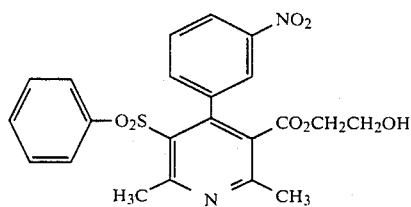

2-Hydroxyethyl 2,6-dimethyl-4-(3-nitrophenyl)-3-phenylsulphonylpyridine-5-carboxylate, of melting point 150° C., was obtained in analogy to Example 1 by reaction of 2-hydroxyethyl 1,4-dihydro-2,6-dimethyl-4-(3-nitrophenyl)-3-phenylsulphonylpyridine-5-carboxylate with nitric acid.

Yield 41% of theory

Example 47

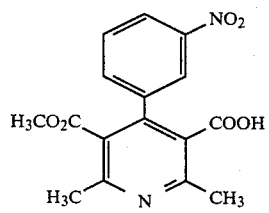

2,6-Dimethyl-4-(3-nitrophenyl)pyridine-3,5-dicarboxylic acid monomethyl ester, of melting point 202° C., was obtained in analogy to Example 11 by reaction of dimethyl 2,6-dimethyl-4-(3-nitrophenyl)pyridine-3,5-dicarboxylate with methanolic potassium hydroxide solution.

Yield 65% of theory.

Example 48

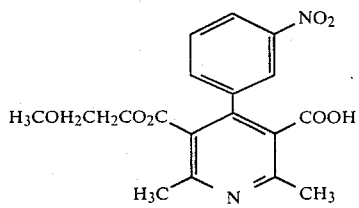

2,6-Dimethyl-4-(3-nitrophenyl)pyridine-3,5-dicarboxylic acid mono(2-methoxyethyl) ester, of melting point 191° C., was obtained in analogy to Example 11 by reaction of bis(2-methoxyethyl) 2,6-dimethyl-4-(3-nitrophenyl)pyridine-3,5-dicarboxylate with methoxyethanolic potassium hydroxide solution.

Yield 58% of theory.

Example 49

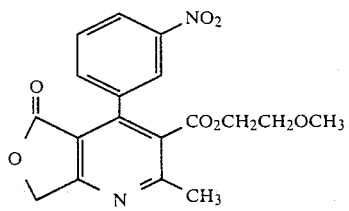

2-Methoxyethyl 5,7-dihydro-2-methyl-4-(3-nitrophenyl)-5-oxofuro[3,4-b]pyridine-3-carboxylate, of melting point 114° C., was obtained in analogy to Example 9 by reaction of 2-methoxyethyl 1,4,5,7-tetrahydro-2-methyl-4-(3-nitrophenyl)-5-oxofuro[3,4-b]pyridine-3-carboxylate with chromium(VI) oxide in glacial acetic acid.

Yield 75% of theory.

Example 50

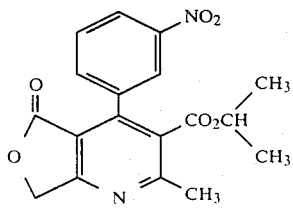

Isopropyl 5,7-dihydro-2-methyl-4-(3-nitrophenyl)5-oxofuro[3,4-b]pyridine-3-carboxylate, of melting point 181° C., was obtained in analogy to Example 9 by reaction of isopropyl 1,4,5,7-tetrahydro-2-methyl-4-(3-nitrophenyl)-5-oxofuro[3,4-b]pyridine-3-carboxylate with chromium(VI) oxide in glacial acetic acid.

Yield 80% of theory.

Example 51

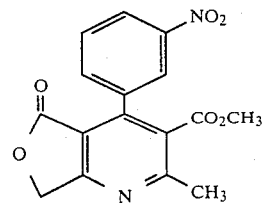

Methyl 5,7-dihydro-2-methyl-4-(3-nitrophenyl)-5-oxofuro[3,4-b]pyridine-3-carboxylate, of melting point 214° C., was obtained in analogy to Example 9 by reaction of methyl 1,4,5,7-tetrahydro-2-methyl-4-(3-nitrophenyl)-5-oxofuro[3,4-b]pyridine-3-carboxylate with chromium(VI) oxide in glacial acetic acid.

Yield: 78% of theory.

Example 52

Potassium salt of 2-hydroxymethyl-6-methyl-4-(3-nitrophenyl)pyridine-3,5-dicarboxylic acid 5-(2-hydroxyethyl) ester.

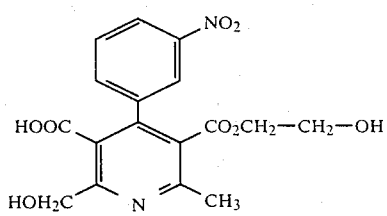

24 g (50 mmols) of 5-(2-acetoxyethyl) 3-ethyl 2-acetoxymethyl-6-methyl-4-(3-nitrophenyl)pyridine-3,5-dicarboxylate were dissolved in 120 ml of 1,2-dimethoxyethane and, after careful addition of a solution of 6.2 g of potassium hydroxide in 120 ml of water, was stirred at room temperature for two hours. The mixture was then extracted several times with methylene chloride, the aqueous phase was evaporated to dryness in vacuo and the residue was recrystallized from isopropanol.

Melting point 223° C. Yield 3.6 g (17% of theory).

Example 53

2-Hydroxyethyl 5,7-dihydro-2-methyl-4-(3-nitrophenyl)-5-oxofuro[3,4-b]pyridine-3-carboxylate

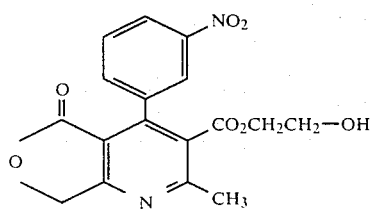

4 g of potassium salt of 2-hydroxymethyl-6-methyl-4-(3-nitrophenyl)pyridine-3,5-dicarboxylic acid 5-(2-hydroxyethyl) ester (Example 52) were dissolved in 4 ml of water and acidified with concentrated hydrochloric acid. After standing overnight at room temperature, the mixture was diluted with water, the oil which separated out was extracted with methylene chloride, the organic extracts, after drying over sodium sulphate, were evaporated in vacuo and the residue was recrystallized from isopropanol, melting point 130° C.

Yield: 2.3 g (64% of theory).

It is understood that the specification and examples are illustrative but not limitative of the present invention and that other embodiments within the spirit and scope of the invention will suggest themselves to those skilled in the art.

We claim:

1. A method of controlling damage to the central nervous system of a patient requiring such treatment which comprises administering to such patient a central nervous system-controlling effective amount of a pyridine derivative of the formula

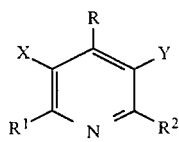

in which

R represents an aryl radical or a thienyl, furyl, pyrryl, imidazolyl, oxazolyl, isoxazolyl, thiazolyl, benzimidazolyl, benzoxazolyl, benzisoxazolyl, and benzoxadiazolyl radical, the aryl radical and the heterocycles optionally containing 1 to 2 identical or different substituents from the group comprising phenyl, alkyl, alkoxy, alkylene, dioxyalkylene, halogen, trifluoromethyl, polyfluoroalkoxy, nitro, cyano, azido or $SO_m$-alkyl (m=0 to 2), $R^1$ and $R^2$ are identical or different and represent hydrogen, a straight-chain or branched alkyl radical, an aryl radical or an aralkyl radical or represent an acyloxyalkyl or a hydroxyalkyl group, or represent an alkylene chain, which, together with X or Y, forms a 5 to 7-membered ring which contains a carbonyl group and optionally an oxygen or nitrogen atom, and X and Y are identical or different and represent the nitrile group or represent the radical —CO—$R^3$, $R^3$ representing a straight-chain, branched or cyclic alkyl radical, an aryl radical or an aralkyl radical, or X and Y represent the group —COO$R^4$, $R^4$ representing a hydrogen atom, a straight-chain, branched or cyclic, saturated or unsaturated hydrocarbon radical, which is optionally interrupted by an oxygen atom in the chain and/or is optionally substituted by halogen, cyano, hydroxyl, acyloxy, pyridyl, aryl or aryloxy, it being possible for the aryl groups in turn to be substituted by alkyl, fluorinated alkyl, alkoxy, halogen or nitro, or by an amino group which is optionally substituted by two identical or different substituents from the group comprising alkyl, aryl or aralkyl, or X and Y represent the group —$SO_2R^5$, $R^5$ representing a lower alkyl radical or a phenyl radical optionally substituted by halogen, trifluoromethyl, alkoxy or alkyl, or a salt thereof.

2. The method according to claim 1, in which

R represents a phenyl or naphthyl radical or represents a thienyl, furyl, pyrryl, imidazolyl, oxazolyl, isoxazolyl, thiazolyl, benzimidazolyl, benzoxazolyl, and benzisoxazolyl radical, the phenyl or naphthyl ring and the heterocycles optionally containing 1 to 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, tri-, tetra- or pentamethylene, dioxymethylene, dioxyethylene, fluorine, chlorine, bromine or iodine, trifluoromethyl, trifluoromethoxy, difluoromethoxy, tetrafluoroethoxy, nitro, cyano, azido or $SO_m$-alkyl, wherein m denotes a number from 0 to 2 and alkyl 1 to 4 carbon atoms, $R^1$ and $R^2$ are identical or different and represent hydrogen or represent a straight-chain or branched alkyl radical having 1 to 8 carbon atoms or represent a phenyl radical or a benzyl radical or represent the acetoxymethyl or 2-acetoxyethyl radical or represent a hydroxyalkyl group having up to 4 carbon atoms in the alkyl moiety, or represent an alkylene chain, which is optionally substituted by alkyl (1 to 4 C atoms), having 1 to 3 carbon atoms, which, together with X or Y, form a 5 to 7-membered ring, which contains a carbonyl group and optionally an oxygen or nitrogen atom, the nitrogen optionally still carrying a hydrogen atom or a lower alkyl radical (1 to 4 C atoms), and X and Y are identical or different and represent the nitrile group or represent the radical —$COR^3$, $R^3$ representing a straight-chain, branched or cyclic alkyl radical having 1 to 8 carbon atoms, or the phenyl group or the benzyl group, or X and Y represent the group —$COOR^4$, $R^4$ representing a hydrogen atom, a straight-chain, branched or cyclic, saturated or unsaturated hydrocarbon radical having up to 12 carbon atoms, which is optionally interrupted by one oxygen atom in the chain and/or is optionally substituted by fluorine, chlorine, bromine, cyano, hydroxyl, acetoxy, α-, β- or γ-pyridyl, phenyl, phenoxy or naphthoxy, it being possible for the aryl groups in turn to be substituted by lower alkyl (1 to 4 C atoms), trifluoromethyl, lower alkoxy (1 to 4 C atoms), fluorine or chlorine or nitro, or by an amino group, which is optionally substituted by two identical or different substituents from the group comprising alkyl having 1 to 2 carbon atoms, phenyl or benzyl, or X and Y represent the group —$SO_2R^5$, $R^5$ representing a lower alkyl radical having 1 to 8 carbon atoms or a phenyl group, which is optionally substituted by fluorine, chlorine, trifluoromethyl, alkyl or alkoxy having, in each case, 1 to 4 carbon atoms.

3. The method according to claim 1, in which

R represents phenyl or pyridyl, the phenyl radical optionally being substituted once or twice by nitro, cyano, trifluoromethyl, fluorine, chlorine, bromine, iodine, alkyl, alkoxy, alkylmercapto having, in each case, 1 to 2 C atoms in the alkyl and alkoxy radicals, $R^1$ and $R^2$ are identical or different and represent, in each case, hydrogen or an alkyl radical having 1 to 4 carbon atoms, which is optionally substituted by hydroxyl, or $R^1$ together with X or $R^2$ together with Y together form a 5 to 7-membered ring, which is interrupted by carbonyl and optionally by oxygen and/or NH and X and Y are identical or different and each represent a nitrile group or X and Y represent the radical —COR$^3$, R$^3$ denoting an alkyl radical having 1 to 4 carbon atoms, phenyl or benzyl or X and Y represent the group —COOR$^4$, R$^4$ denoting hydrogen, a straight-chain, branched or cyclic saturated or unsaturated hydrocarbon radical having up to 10 carbon atoms, which is optionally interrupted by 1 oxygen atom in the chain and/or is optionally substituted by hydroxyl, fluorine, chlorine, bromine, cyano, acetoxy, pyridyl, phenyl or phenoxy, it being possible for the phenyl groups in turn to be optionally substituted by fluorine, chlorine, trifluoromethyl, nitro, alkyl having 1 to 4 C atoms or alkoxy having 1 to 4 C atoms, or X and Y represent the group —SO$_2$R$^5$, R$^5$ representing an alkyl radical having 1 to 4 carbon atoms or a phenyl group, which is optionally substituted by fluorine, chlorine, trifluoromethyl, alkyl or alkoxy having, in each case, 1 to 2 carbon atoms.

4. The method according to claim 1, wherein the central nervous system disorder is due to ischaemia or hypoxia.

5. The method according to claim 1, wherein such compound is 2-hydroxyethyl isopropyl 2,6-dimethyl-4-(3-nitrophenyl)-pyridine-3,5-dicarboxylate of the formula

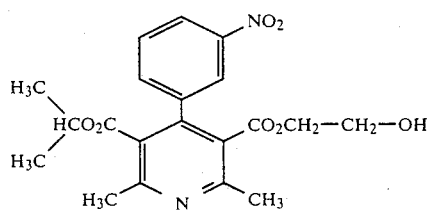

or a salt thereof.

6. The method according to claim 1, wherein such compound is 2-cyanoethyl 3-acetyl-2,6-dimethyl-4-(3-nitrophenyl)-pyridine-5-carboxylate of the formula

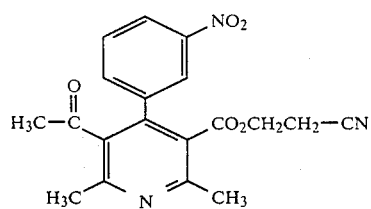

or a salt thereof.

7. The method according to claim 1, wherein such compound is 2-hydroxyethyl methyl 2,6-dimethyl-4-(3-nitrophenyl) pyridine-3,5-dicarboxylate of the formula

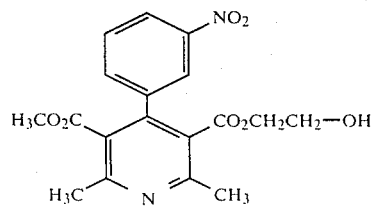

or a salt thereof.

8. The method according to claim 1, wherein such compound is 2-cyanoethyl methyl 2,6-dimethyl-4-(3-nitrophenyl) pyridine-3,5-dicarboxylate of the formula

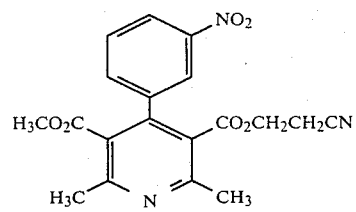

or a salt thereof.

9. The method according to claim 1, wherein such compound is methyl 2-(3-trifluoromethylphenoxy) 2,6-dimethyl-4-(3-nitrophenyl) pyridine-3,5-dicarboxylate of the formula

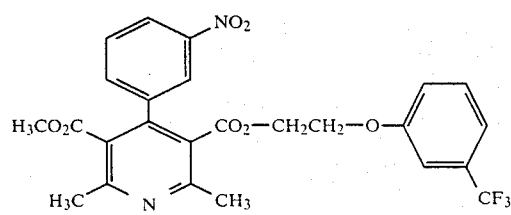

or a salt thereof.

10. A method according to claim 1, wherein such compound is ethyl 2-hydroxyethyl 2,6-dimethyl-4-(2-trifluoromethylphenyl) pyridine-3,5-dicarboxylate of the formula

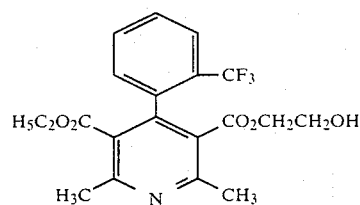

or a salt thereof.

11. A method according to claim 1, wherein such compound is 2-hydroxymethyl-6-methyl-4-(3-nitrophenyl) pyridine-3,5-dicarboxylic acid 5-(2-hydroxyethyl) ester of the formula

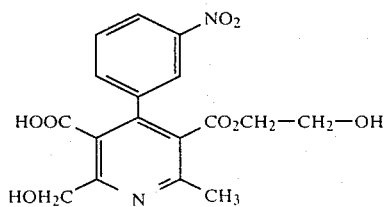

of a salt thereof.

12. The method according to claim 1, wherein such compound is 2-hydroxyethyl 5,7-dihydro-2-methyl-4-(3-nitrophenyl)-5-oxofuro[3,4-b]pyridine-3-carboxylate of the formula

29
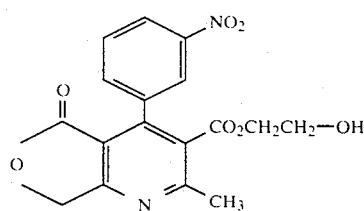
or a salt thereof.
* * * * *
30
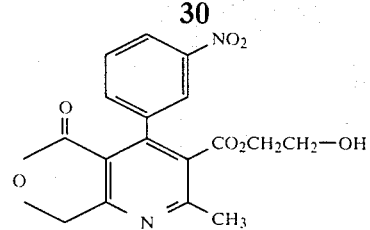
or a salt thereof.
* * * * *

UNITED STATES PATENT AND TRADEMARK OFFICE
CERTIFICATE OF CORRECTION

PATENT NO. : 4,497,821

DATED : February 5, 1985

INVENTOR(S) : Egbert Wehinger, et al

It is certified that error appears in the above-identified patent and that said Letters Patent is hereby corrected as shown below:

| | |
|---|---|
| Col. 1, line 55 | Delete "quinoxazolyl" and substitute --quinoxalyl-- |
| Col. 4, line 36 | After "4" insert --C-- |
| Col. 6, line 12 | Delete "hypoxia" and substitute --hypoxic-- |
| Col. 10, line 20 | Delete "mmoles" and substitute --mmols-- |
| Col. 12, line 30 | Delete bottom left of formula and substitute |
| Col. 23, line 60 | Before "5" (2nd occurr) insert-- |
| Col. 30, lines 1-10 | Cancel all matter therein |

Signed and Sealed this

Twenty-third Day of July 1985

[SEAL]

Attest:

DONALD J. QUIGG

Attesting Officer     Acting Commissioner of Patents and Trademarks